United States Patent
Avila

(10) Patent No.: US 7,799,355 B2
(45) Date of Patent: Sep. 21, 2010

(54) NATURAL TOPICAL COMPOSITIONS FOR THE PREVENTION AND TREATMENT OF DIAPER RASHES AND RELATED CONDITIONS

(75) Inventor: Rafael Avila, Farmingdale, NY (US)

(73) Assignee: Natural Organics, Inc., Melville, NY (US)

( * ) Notice: Subject to any disclaimer, the term of this patent is extended or adjusted under 35 U.S.C. 154(b) by 0 days.

(21) Appl. No.: 12/455,726

(22) Filed: Jun. 5, 2009

(65) Prior Publication Data
US 2009/0247622 A1 Oct. 1, 2009

(51) Int. Cl.
*A61K 36/45* (2006.01)
*A61K 8/02* (2006.01)

(52) U.S. Cl. .................. 424/732; 424/401; 514/865

(58) Field of Classification Search .................. None
See application file for complete search history.

(56) References Cited

FOREIGN PATENT DOCUMENTS

JP        2002003389 A  *  1/2002

OTHER PUBLICATIONS

Prior, R.L. et al. J. Agric. Food Chem., 2001, 49 (3), pp. 1270-1276. Identification of Procyanidins and Anthocyanins in Blueberries and Cranberries (*Vaccinium* Spp.) Using High-Performance Liquid Chromatography/Mass Spectrometry.*
Vvedenskaya, I.O. et al. Plant Science, 2004, 167(5): 1043-1054. Flavonoid composition over fruit development and maturation in American cranberry, *Vaccinium macrocarpon* Ait.*

* cited by examiner

*Primary Examiner*—Michele C. Flood
(74) *Attorney, Agent, or Firm*—Abelman, Frayne & Schwab

(57) ABSTRACT

The treatment and prevention of skin irritations, including diaper rash, is facilitated with the topical application of cranberry anthocyanins in a cosmetically acceptable vehicle.

4 Claims, No Drawings

NATURAL TOPICAL COMPOSITIONS FOR THE PREVENTION AND TREATMENT OF DIAPER RASHES AND RELATED CONDITIONS

BACKGROUND OF THE INVENTION

1. Field of the Invention

This invention relates to topical compositions for the treatment of skin irritation and, more particularly, to anthocyanin-containing compositions for the treatment of diaper rash.

2. Background of the Invention and Related Art

Diaper rash (also referred to as diaper dermatitis or incontinence dermatitis) is a generic term applied to rashes seen in the diaper area (genital, buttocks and thighs, or any area of skin that is covered by a diaper-like dressing) that may be caused by a variety of skin disorders. Diaper dermatitis develops when skin is exposed to prolonged wetness, increased skin pH caused by urine and feces, with the resulting breakdown of the stratum corneum, or outermost layer of the skin. In adults, the stratum corneum is composed of 25 to 30 layers of flattened dead keratinocytes, which are continuously shed and replaced from below. These dead cells are interlayered with lipids secreted by the stratum granulosum just underneath, which help to make this layer of the skin a waterproof barrier. The stratum corneum's function is to reduce water loss, repel water, protect deeper layers of the skin from injury and to repel microbial invasion of the skin. In infants, this layer of the skin is much thinner and more easily disrupted.

It is generally accepted that various combinations of factors, and not a single causative factor, causes diaper rash. However, certain factors appear to be far more prevalent as causal agents than others. The most prominent factors are ammonia from urine and its increase of the pH of the skin, bacterial growth and the metabolic byproducts of such growth, yeast growth, including *Candida albicans*, and their metabolic byproducts, and excess moisture.

The use of herbal remedies and ointments for the soothing or treatment of diaper rashes is known in the prior art. For example, U.S. Pat. No. 6,627,178, the disclosure of which is incorporated herein by reference, discloses an ointment composition containing calendula, chamomile and/or comfrey for the treatment of diaper rashes. Another example of the use of herbal remedies in ointments for the treatment of diaper rashes is U.S. Pat. No. 6,419,963, the disclosure of which is incorporated herein by reference, which discloses a composition containing beeswax, olive oil, beta-sitosterol and the herb *Coptis chinensis* Franch.

However, neither of the aforementioned patents yield the benefits achieved by the current invention, which provides an economical, all-natural product that provides relief from diaper rash, as well as other skin irritations.

All references to "Cranberry" hereinafter encompass cranberry, cranberry extract, cranberry concentrate, cranberry juice, cranberry juice concentrates, in all forms, including by way of examples and not by way of limitation, liquid, solid, powdered, dehydrated, or extracted using any of the currently available production methods.

SUMMARY OF THE INVENTION

The present invention addresses a number of problems associated with previously known diaper rash treatments by providing compositions which include anthocyanins which contribute to the treatment and/or prevention of diaper rash. While previous treatments and compositions required multiple ingredients to achieve a) a reduction of pH, b) a reduction of moisture and c) a reduction of irritant microbes and/or irritant microbial byproducts, the inclusion of at least one anthocyanin in the composition of the present invention achieves all of these objectives. And given that *vaccinium macrocarpon* known colloquially as cranberry, which contains the preferred anthocyanins for use in the present invention is widely abundant and inexpensive, the present invention, achieves the aforementioned objectives in a very cost-effective manner.

The present invention is primarily intended for use on or around the affected skin of the diaper area in both infants and toddlers and incontinent adults. This includes, but is not limited to, the buttocks, genitals, lower abdomen and the thigh folds.

Cranberry and/or cranberry extract is naturally acidic and therefore naturally helps to lower skin pH. Cranberry has also been found to contain as much as 12% fiber (DUKE1992A), and is a known moisture adsorbent. And, most importantly, numerous studies (Di Martino et al. 2006, Firon et al. 1987; Jepson et al. 2004; Howell et al. 2005; Raz et al. 2004; Tsukada et al. 1994; Turner et al. 2005; Zafriri et al., 1989; Zhang et al. 2005) have shown that cranberry and/or cranberry extracts inhibit the adhesion of yeast and bacteria to epithelial surfaces. Such inhibition of adhesion inhibits the growth of yeast and bacteria (as well as other microorganisms). With reduced adhesive capacity, microorganisms are more easily removed through common practices of diaper changing, wiping and general good hygiene. Thus, cranberry and/or cranberry extract contributes many attributes, which effectively combat many of the causal factors of diaper rash.

The present invention includes all known topical delivery media or mechanisms, including by way of example, and not by way of limitation, lotions, creams, ointments, sprays, dressings, or other methods of topical application. Exemplary thereof would be any of the known ointment or lotion media with a low level of skin irritation.

The present invention may include cranberry alone, or it may include cranberry as part of a more comprehensive formulation, including other ingredients. The following formulation is a representative embodiment of such other ingredients and it is not intended to limit the scope of the invention.

Zinc oxide (Functions as a barrier material);
cod liver oil (skin conditioning agent-source of vitamins A and D);
lavender (Fragrance);
chamomile (Fragrance);
natural vitamin E (skin conditioning agent);
lanolin (skin conditioning agent);
fragrance
petrolatum (functions as a barrier material);
talc; and
purified water.

The present invention incorporates a concentration of at least about 16 ppb of Cranberry- or other *vaccinium*-derived anthocyanins. The use of higher concentrations, up to about 50% by weight of the composition, can be employed advantageously with the upper limit being dictated by the benefit realized to the patient.

It has been found that it is primarily the proanthocyanins and anthocyanins in *vaccinium* genus, including cranberry (*Vaccinium macrocarpon*), that impart the anti-microbial-adhesion activity. Accordingly, juices, concentrates, and extracts from all members of the *vaccinium* genus can be employed to advantage, with cranberry being preferred.

Cranberry anthocyanins commonly occur in cranberry fruit and juice in the range of 18 mg per 100 g, or 0.018% (Zhou and Singh, 2004). A medium containing 11.25 parts per million (0.001%) cranberry fruit or cranberry juice will contain 16 ppb of cranberry anthocyanins, and thus contain a concentration of cranberry anthocyanins sufficient to impart anti-adhesion microbial activity.

Although the aforesaid embodiment of this invention focuses on diaper rash, it may also be used to advantage in the treatment of any of the following conditions as they may relate to, or be exacerbated by, bacterial adhesion:

acne, actinic keratosis, athlete's foot, aquagenic pruritus, atopic dermatitis, bed sore, Behcet's disease, blepharitis, boils, Bowen's disease, bullous pemphigoid, canker sore, carbuncles, cellulitis, chloracne, chronic dermatitis of the hands and feet, cold sores, contact dermatitis, creeping eruption, dandruff, dermatitis, dermatitis herpetiformis, diaper rash, dyshidrosis, eczema, epidermolysis bullosa, erysipelas, erythroderma, Ferguson's disease, friction blister, hidradenitis suppurativa, hyperhidrosis, ichthyosis, impetigo, jock itch, keloid, keratosis pilaris, lichen planus, lichen simplex chronicus, lymphadenitis, melasma, miliaria, molluscum contagiosum, nummular dermatitis, pediculosis, pemphigus, perioral dermatitis, photoallergy, photosensitivity, pityriasis rosea, pityriasis rubra pilaris, porphyria, psoriasis, Raynaud's disease, ringworm, rosacea, scabies, scleroderma, sebaceous cyst, seborrheic keratosis, seborrhoeic dermatitis, shingles, skin tags, spider veins, stasis dermatitis, tinea barbae, tinea capitis, tinea corporis, tinea cruris, tinea pedis, tinea unguium, tinea versicolor, tinea, tungiasis, urticaria, and warts.

DETAILED DESCRIPTION OF THE INVENTION

Preferred embodiments of the invention are described in the form of a cream, a powder and a baby wipe, with the percentage of ingredients present being listed in descending order from the highest to the lowest. In each embodiment, cranberry extract is included at 0.01%, by weight, of the total composition.

Cream Form

Aloe Barbadensis Leaf Juice, Zinc Oxide (included at 10% by weight), Beeswax, Benzyl Alcohol, Coconut Oil, Cod liver Oil, Dimethicone, Fragrance, Glyceryl Oleate, Mineral Oil, Ozokerite, Paraffin, Propylene Glycol, Purified Water, Red Ferric Oxide, Sorbitol, cranberry extract (*Vaccinium macrocarpon* fruit extract containing 0.2-0.8% anthocyanins, and/or related anthocyanosides).

Powder Form

Corn starch, zinc oxide (included at 10% by weight), ferric oxide, fragrance, cranberry extract (*Vaccinium magrocarpon* fruit extract containing 0.2-0.8% anthocyanins, and/or related anthocyanosides), tricalcium phosphate.

Disposable Baby Wipe Form

Water, Glycerin, Aloe Vera, Tocopheryl Acetate (Vitamin E), Polysorbate 20, Cranberry Extract, Potassium Sorbate, Tartaric Acid, Fragrance.

Accordingly, it will be appreciated that the present invention has been described with reference to particular preferred embodiments that are now contemplated. However, the invention is not limited to the embodiments disclosed herein and it will be appreciated that numerous modifications and other embodiments may be devised by those skilled in the art. Therefore, it is intended that the appended claims cover all such modifications and embodiments that fall within the spirit and scope of the present invention.

What is claimed is:

1. A method for treating or preventing diaper rash in humans comprising applying a topical pharmaceutical composition, which includes a therapeutically effective quantity of a cranberry anthocyanins in a cosmetically acceptable carrier, to an irritated skin surface to form a protective coating thereon.

2. The method of claim 1, wherein the cosmetically acceptable carrier is in the form of a powder, concentrate, extract, lotion, cream, ointment or spray.

3. The method of claim 2, wherein the carrier contains from about 16 parts per billion to about 50% by weight of cranberry anthocyanins based on the total weight of the composition.

4. The method of claim 3, wherein the carrier contains about 0.2% to 0.8%, by weight, of a cranberry anthocyanin.

* * * * *

UNITED STATES PATENT AND TRADEMARK OFFICE
CERTIFICATE OF CORRECTION

PATENT NO. : 7,799,355 B2  
APPLICATION NO. : 12/455726  
DATED : September 21, 2010  
INVENTOR(S) : Rafael Avila Page 1 of 1

It is certified that error appears in the above-identified patent and that said Letters Patent is hereby corrected as shown below:

Title Page

Insert

-- Related U.S. Application Data

(60) Provisional application No. 60/872,712, filed on Dec. 4, 2006 --

Signed and Sealed this

Twentieth Day of March, 2012

David J. Kappos
*Director of the United States Patent and Trademark Office*